(12) United States Patent
Chien et al.

(10) Patent No.: US 8,765,933 B2
(45) Date of Patent: Jul. 1, 2014

(54) ASYNTHESIS OF β-NUCLEOSIDES

(75) Inventors: Chungsun Chien, Taoyuan County (TW); Pin-Shu Chien, Taipei (TW); Chan-Kou Hwang, Taipei (TW)

(73) Assignee: PharmaEssentia Corp., Taipei (TW)

( * ) Notice: Subject to any disclaimer, the term of this patent is extended or adjusted under 35 U.S.C. 154(b) by 148 days.

(21) Appl. No.: 13/435,607

(22) Filed: Mar. 30, 2012

(65) Prior Publication Data

US 2012/0259106 A1    Oct. 11, 2012

Related U.S. Application Data

(60) Provisional application No. 61/472,796, filed on Apr. 7, 2011.

(51) Int. Cl.
*C07H 21/00* (2006.01)

(52) U.S. Cl.
USPC ............. 536/25.3; 536/25.31; 536/124

(58) Field of Classification Search
None
See application file for complete search history.

(56) References Cited

U.S. PATENT DOCUMENTS

| | | |
|---|---|---|
| 4,526,988 A | 7/1985 | Hertel |
| 4,808,614 A | 2/1989 | Hertel |
| 5,223,608 A | 6/1993 | Chou et al. |

FOREIGN PATENT DOCUMENTS

WO    WO2009/061894    5/2009

OTHER PUBLICATIONS

Renate Van well et al.; "Iodine Promoted Glycosylation with Glycosyl Iodies: [alpha]-Glycoside Synthesis"; Journal of Carbohydrate Chemistry; 24(4-6); 463-474 (2005).
XP002675549 "Iodine Clock Reaction" Wikipedia (2010); http://en.widipedia.org/wiki/Idoine_clock_reaction.
Chou et al.; "Stereospecific synthesis of 2-deoxy-2,2-difluororibonolactone and its use in the preparation of 2'-deoxy-2',2'-difluoro-β-D-ribofuranosyl pyrimidine nucelosies: the key role of selective crystallization"; Synthesis, 565-570 (1992).

*Primary Examiner* — Patrick Lewis
(74) *Attorney, Agent, or Firm* — Cesari and McKenna, LLP

(57) ABSTRACT

A process of stereoselectively synthesizing β-nucleoside, e.g., 2'-deoxy-2,2'-difluorocytidine, is described. The process includes reacting a tetrahydrofuran compound of the following formula:

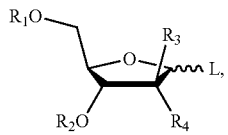

in which wherein $R_1$, $R_2$, $R_3$, $R_4$, and L as defined in the specification, with a nucleobase derivative in the presence of an oxidizing agent.

22 Claims, No Drawings

A SYNTHESIS OF β-NUCLEOSIDES

CROSS-REFERENCE TO RELATED APPLICATIONS

This application claims the benefit of U.S. Provisional Application No. 61/472,796, filed on Apr. 7, 2011. The contents of the application are hereby incorporated by reference in its entirety.

BACKGROUND

2'-Deoxynucleosides and their analogues are therapeutically important agents. For example, gemcitabine, i.e., 2'-deoxy-2,2'-difluorocytidine, can be used to treat viral infection and cancer. See, e.g., U.S. Pat. Nos. 4,526,988 and 4,808,614.

In general, 2'-deoxynucleosides each have more than one chiral center and can occur as multiple stereoisomers. Not all stereoisomers are therapeutically active. Several stereoselective synthetic routes for 2-deoxy-β-nucleosides have been developed. None of them are satisfactory.

There is a need to develop a more effective route for stereoselectively synthesizing 2'-deoxynucleosides.

SUMMARY

One aspect of this invention relates to a process of synthesizing a β-nucleoside compound of formula (I):

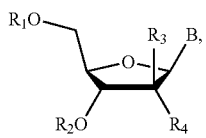
(I)

in which each of $R_1$ and $R_2$, independently, is H, alkyl, aryl, aralkyl, alkyldiarylsilyl, trialkylsilyl, triarylsilyl, RC(O)—, RR'NC(O)—, ROC(O)—, RC(S)—, RR'NC(S)—, or ROC(S)—; each of R and R', independently, being H, alkyl, aryl, cycloalkyl, heterocycloalkyl, or heteroaryl; each of $R_3$ and $R_4$, independently, is H or fluoro; and B is

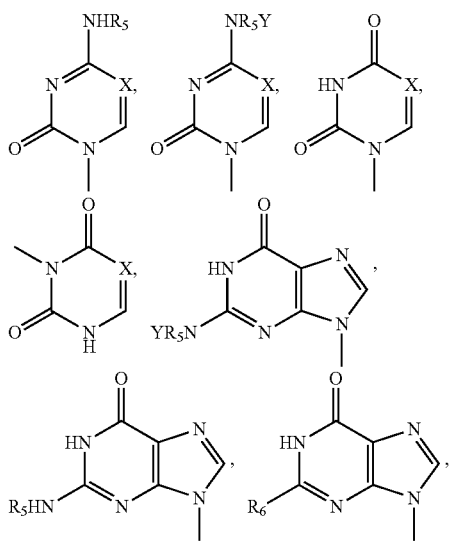

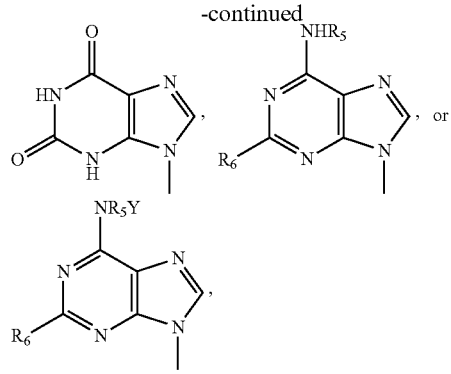

in which $R_5$ is H, alkyl, or aryl; $R_6$ is H, alkyl, alkenyl, halo, or aryl; X is N or C—R", R" being H, alkyl, alkenyl, halo, or aryl; and Y is an amino protecting group. The process includes reacting, in the presence of an oxidizing agent, a tetrahydrofuran compound of formula (II):

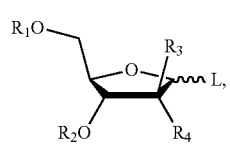
(II)

wherein $R_1$, $R_2$, $R_3$, and $R_4$ are as defined above; L is fluoro, chloro, bromo, or iodio, with a nucleobase derivative of the following formula:

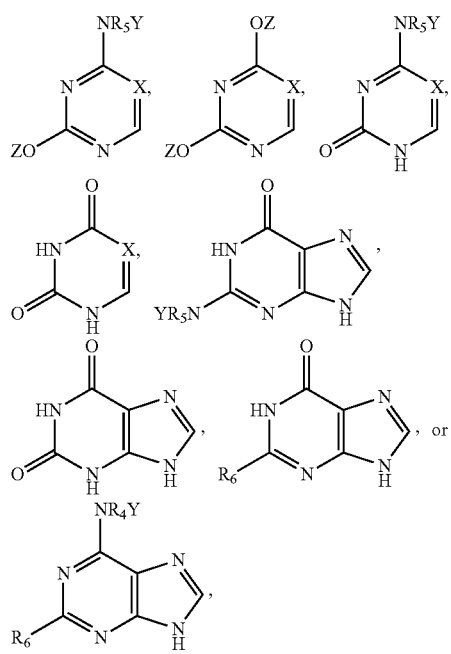

wherein $R_5$, $R_6$, X, and Y are as defined above and Z is a hydroxyl protecting group.

In the above process, the compounds of formulas (I) and (II) may feature that $R_1$ is H, alkyl, aralkyl, alkyldiarylsilyl, trialkylsilyl, triarylsilyl, or RC(O)—; and $R_2$ is RC(O)—, RR'NC(O)—, ROC(O)—, RC(S)—, RR'NC(S)—, or ROC (S)—; each of R and R', independently, being H, alkyl, aryl, cycloalkyl, heterocycloalkyl, or heteroaryl. In some embodiments, the β-nucleoside compound of formula (I) has one or more of the following features: $R_1$ is trityl, $(CH_3)_3C$, alkyldiarylsilyl, trialkylsilyl, or triarylsilyl, $R_2$ is alkyl-C(O)— or aryl-C(O) (e.g., PhC(O)—), and each of $R_3$ and $R_4$ is fluoro; and the compound of formula (II) has one or more of the following features: L is I, and $R_1$ is trityl, $(CH_3)_3C$, alkyldiarylsilyl, trialkylsilyl, or triarylsilyl, $R_2$ is alkyl-C(O)— or aryl-C(O) (e.g., benzoyl); and each of $R_3$ and $R_4$ is fluoro. Of note, the "∿∿" bond shown in formula (II) denotes any configurational relationship between the substituent L and the tetrahydrofuran ring (both of which are also shown in the same formula), e.g., α, β, or a mixture of α and β at any ratio.

The nucleobase derivative used in the above-described process may feature that each of $R_5$ and $R_6$ is trimethylsilyl (TMS).

The oxidizing agent used in the process can be $Br_2$, $H_2O_2$, $O_2$, $Cl_2$, $O_3$, $F_2$, 3-chloroperbezoic acid (MCPBA), azobisisobutyronitrile (AIBN), 2,2,6,6-tetramethylpiperidine 1-oxyl (TEMPO), or a salt including an ion selected from the group consisting of $Fe^{3+}$, $Ce^{4+}$, $Au^{3+}$, $Co^{3+}$, $NO_3^-$, $MnO_4^-$, $Cr_2O_7^{2-}$, $HSO_5^-$, and $S_2O_8^{2-}$. It can also be a peroxide such as hydrogen peroxide or sodium peroxide. The above reaction can be carried out in an organic solvent or solvent mixture (e.g., toluene, acetonitrile, or a mixture of toluene and acetonitrile) at 15-150° C.

An example of the above process is reacting

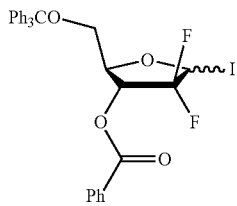

with

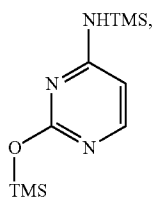

in the presence of $(NH_4)_2S_2O_8$ or $K_2S_2O_8$ to form

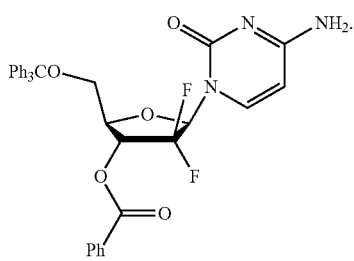

The process of this invention may further include converting the β-nucleoside compound to a compound of formula (III):

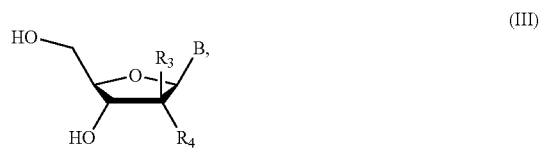

(III)

wherein $R_3$, $R_4$, and B are as defined above.

In the above process, the compound of formula (II), a tetrahydrofuran derivative, can be prepared by reducing a lactone compound of the following formula (IV):

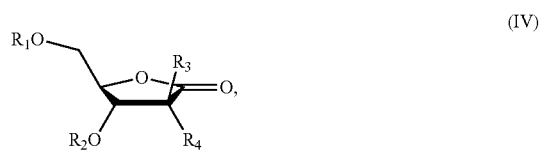

(IV)

wherein $R_3$, $R_4$, and B are as defined above, to a furanose compound of the following formula:

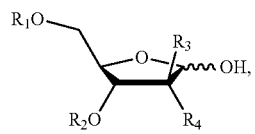

wherein $R_3$, $R_4$, and B are as defined above, and converting the furanose compound to the tetrahydrofuran compound of formula (II). The compound of formula (IV), in turn, can be prepared by first treating with acid a compound of the following formula:

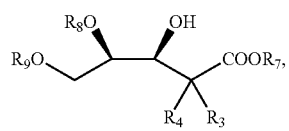

wherein each of $R_3$ and $R_4$, independently, is H or halo; $R_7$ is H, alkyl, aryl, cycloalkyl, heteroalkyl, or hetereoaryl; and each of $R_8$ and $R_9$, independently, is a H or hydroxyl protecting group, or $R_8$ and $R_9$, together, are $C_{1-3}$ alkylene, then reacting the product resulting from the above treatment with a compound of the following formula:

$R_1$-L', wherein $R_1$ is alkyl, aralkyl, alkyldiarylsilyl, trialkylsilyl, triarylsilyl, alkylcarbonyl, or arylcarbonyl; and L' is a leaving group, to produce a compound of formula (V):

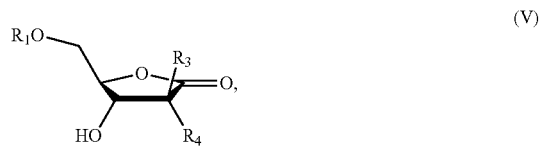

(V)

wherein $R_1$, $R_3$, and $R_4$ are as defined above, and finally protecting the free OH group in the compound of formula (V) with $R_2$. A leaving group can depart, upon direct displacement or ionization, with the pair of electrons from one of its covalent bonds (see, e.g., F. A. Carey and R. J. Sundberg, *Advanced Organic Chemistry*, 3$^{rd}$ Ed. Plenum Press, 1990). Examples of a leaving group include, but are not limited to, methanesulfonate, triflate, p-toluenesulfonate, iodide, bromide, chloride, and trifluoroacetate.

The term "alkyl" refers to a straight or branched hydrocarbon, containing 1-6 carbon atoms. Examples of alkyl groups include, but are not limited to, methyl, ethyl, n-propyl, i-propyl, n-butyl, i-butyl, and t-butyl. The term "alkoxy" refers to an O-alkyl radical. Examples of alkoxy groups include, but are not limited to, methoxy, ethoxyl, and butoxy. The term "alkylene" refers to an alkyl diradical group. Examples of "alkylene" include, but are not limited to, methylene and ethylene.

The term "alkenyl" refers to a straight or branched hydrocarbon having one or more carbon-carbon double bonds. Examples of alkenyl groups include, but are not limited to, ethenyl, 1-butenyl, and 2-butenyl.

The term "aralkyl" refers to an alkyl moiety having one or more aryl substituents. Examples of aralkyl groups include, but are not limited to, benzyl and trityl (i.e., Ph$_3$C).

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl.

The term "alkoxycarbonyl" refers to an alkyl-O-carbonyl radical. Examples of alkoxycarbonyl groups include, but are not limited to, methoxycarbonyl, ethoxycarbonyl, and t-butoxylcarbonyl. The term "aroxycarbonyl" refers to an aryl-O-carbonyl radical. Examples of aroxycarbonyl groups include, but are not limited to, phenoxycarbonyl and 1-naphthalenoxycarbonyl. The term "aminocarbonyl" refers to a (R)(R') N-carbonyl radical in which each of R and R', independently, is H, alkyl, or aryl. Examples of aminocarbonyl groups include, but are not limited to, dimethylaminocarbonyl, methylethylaminocarbonyl, and phenylaminocarbonyl.

Alkyl, aryl, alkenyl, and alkoxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyl, and heterocyclyl, in which the alkyl, alkenyl, alkynyl, alkyloxy, aryl, heteroaryl, cyclyl, and heterocyclyl may be further substituted.

The term "furanose" refers to a five-membered cyclic acetal form of a sugar.

Other features, objects, and advantages of the invention will be apparent from the detailed description and the claims below.

DETAILED DESCRIPTION

This invention relates to an effective process for stereoselectively synthesizing 2'-deoxynucleosides, more specifically, gemcitabine, as well as novel intermediates produced in this process.

Conventional chemical transformations can be used to practice this invention. One skilled person in the art would be able to determine suitable chemical agents, solvents, protecting groups, and reaction conditions for these transformations. Relevant information is described, for example, in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. For illustrative purposes, an embodiment of the process of this invention is described herein.

As outlined in Scheme 1 below, compound 1 of this invention can be synthesized from compound 3, which can be prepared by a known method. See e.g. L. W. Hertel U.S. Pat. No. 4,526,988 or T. S. Chou, et al. Synthesis, 1992, 565-570. Removal of the acetonide in compound 3 can be carried out with trifluoroacetic acid in a mixture of an appropriate organic solvent and water at elevated temperature to afford a mixture of trihydroxy-pentanoate 4,3,5-dihydroxy lactone 5, and trihydroxy-pentanoic acid 6. The mixture is then treated with trityl chloride at a temperature well below 100° C. to provide 5-protected lactone 1 at a high yield. Lactone 1 can be used in a next reaction step without purification.

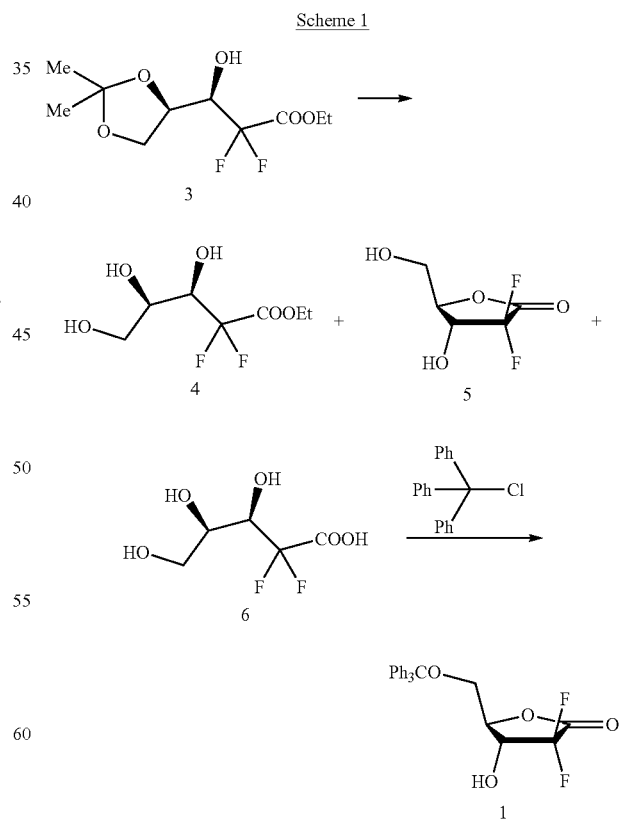

Scheme 1

Scheme 2 below shows a synthetic route to a β-nucleoside compound from compound 1.

Scheme 2

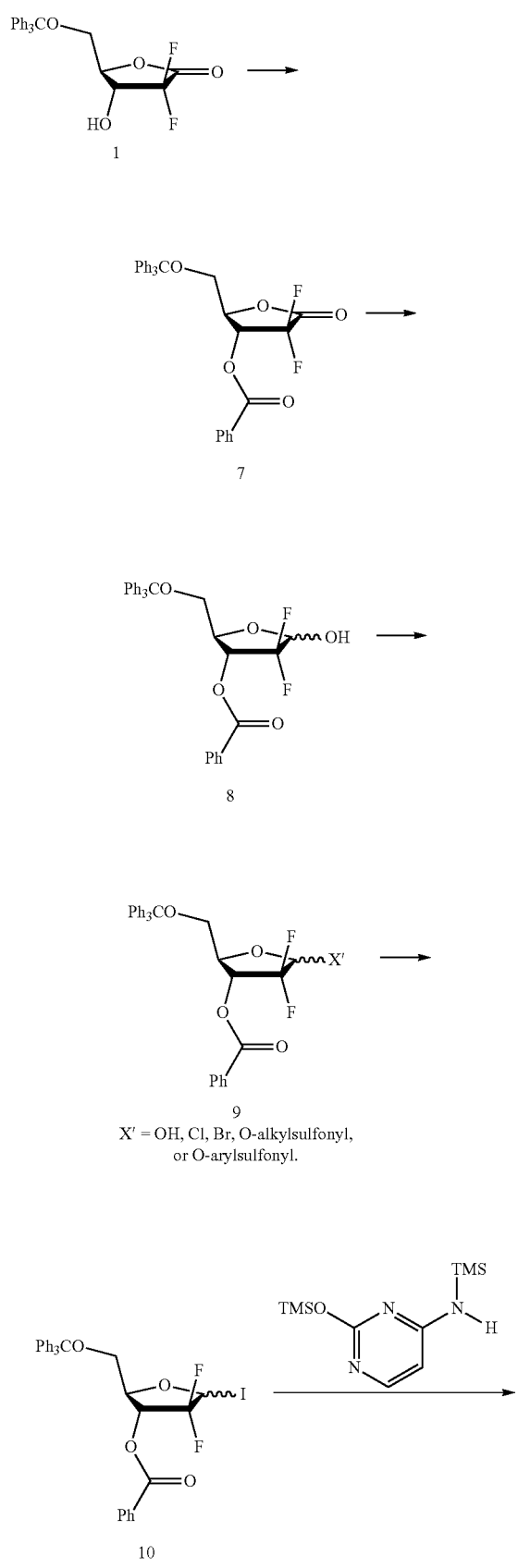

X' = OH, Cl, Br, O-alkylsulfonyl, or O-arylsulfonyl.

The hydroxyl group of compound 1 is first protected to form the corresponding benzoate 7, which is converted to the furanose 8 by a reducing agent. Conversion of compound 8 to iodide 10 can be done in two ways. One is to react furanose 8 with $I_2$ in the presence of a trialkylphosphine or trialkylphosphite and a base. The other is to convert furanose 8 to the corresponding chloride, bromide, alkylsulfonate, and arylsulfonate 9, followed by a reaction between the resulting mesylate and an iodide, such as sodium iodide, lithium iodide, potassium iodide, or tetraalkylammonium iodide, at an elevated temperature. Iodide 10 can then be used to react with a nucleobase, e.g., TMS-protected nucleobase, in the presence of an oxidizing agent, to afford a β-nucleoside 11, which is selectively deprotected to give 3-benzoyl-gemcitabine 2. The selective deprotection of compound 11 can further enrich the β-anomer (i.e., compound 2). Saponification of compound 2 with a base can give rise to gemcitabine. This invention features preparation of β-nucleoside 11 as a major product from an anomeric mixture (i.e., the α-anomer:β-anomer ratio is about 1:1) of Compound 10, an iodide compound. Without being bound by theory, this reaction may undergo the following $S_N1$ mechanism shown in Scheme 3 to obtain the stereochemistry of β-nucleoside 11. A small amount of iodine is produced by oxidizing an iodide ion by an oxidizing agent. The iodide ion can be the iodo group in Compound 10. Alternatively, one can add a catalytic amount of iodide salt to the reaction solution. The resulting iodine is then reacted with un-oxidzied Compound 10 to form a triiodide ion. Upon departure of $I_3^-$, the compound becomes an oxonium intermediate. The oxonium intermediate is stabilized by the ester group at the C-3 position of the tetrahydrofuran ring by forming a six-membered cyclic oxonium. Since the ester group is located at the bottom of the tetrahydrofuran ring, so is the six-membered cyclic oxonium. Consequently, the nucleobase moiety attacks the oxonium from the top of the tetrahydrofuran ring due to minimal steric hindrance, thereby providing β-nucleoside 11.

Scheme 3

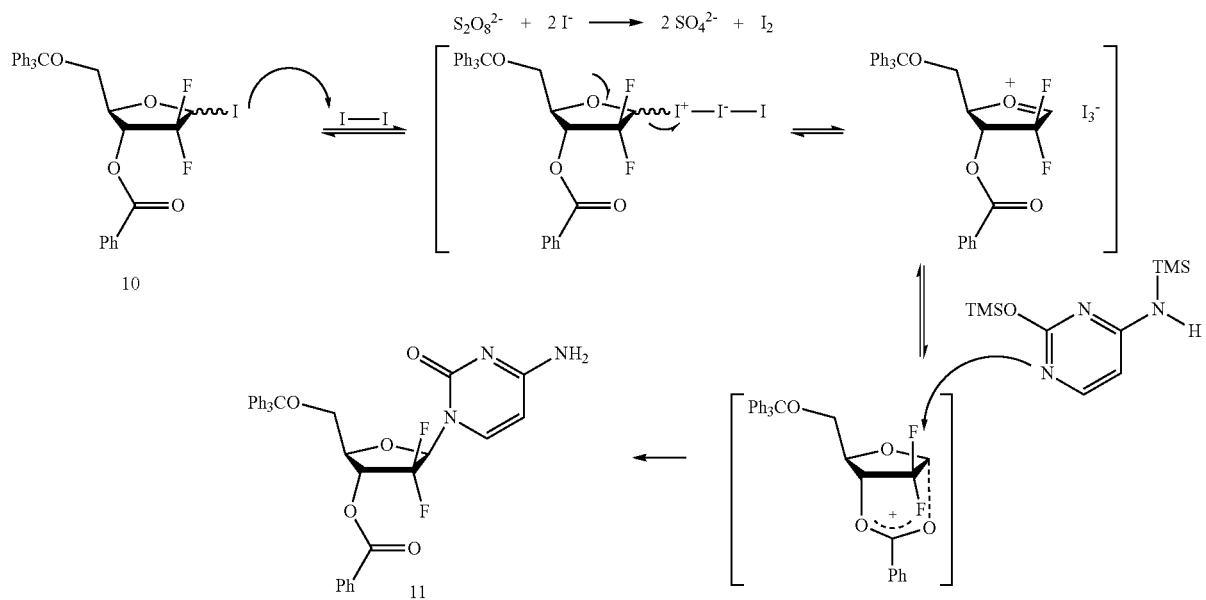

The oxidation of the iodo group is essential to formation of a β-nucleoside compound. It can be carried out by using an oxidizing agent having a higher oxidation/reduction potential)($E^0$) than that of iodine. Examples of such an oxidizing agent include, but are not limited to, $Br_2$, $H_2O_2$, $O_2$, $Cl_2$, $O_3$, $F_2$, MCPBA, AIBN, TEMPO, and various oxidizing ions (e.g., $Fe^{3+}$, $Ce^{4+}$, $Au^{3+}$, $Co^{3+}$, $NO_3^-$, $MnO_4^-$, $Cr_2O_7^{2-}$, $HSO_5^-$ and $S_2O_8^{2-}$). Of note, if a chloride or bromide compound is used in place of an iodide compound (i.e., Compound 10), one needs to use an oxidizing agent having a higher oxidation/reduction potential)($E^0$) than that of chlorine or bromine. Oxidation/reduction potentials of various oxidizing agents are well known in the art. See, e.g., Vanýsek, Petr "Electrochemical Series", in *Handbook of Chemistry and Physics: 90th Edition*, 2009 (Chemical Rubber Company).

The solvent used to conduct this reaction can be organic solvent, preferably selected from those that dissolve Compound 10. Examples include, but are not limited to toluene, acetonitrile, benzene, hexane, acetone, DMSO, dichloromethane, or a mixture thereof. For instance, the reaction can be conducted in toluene, acetonitrile, or a mixture of toluene and acetonitrile.

To practice this invention, protection and deprotection techniques are needed. For example, schemes show use of hydroxyl and amino protecting groups in synthesizing gem-citabine. Namely, the furanose shown above contains two hydroxyl protecting groups and the nucleobase also shown above contains an amino protecting group. Protecting groups refer to those that, upon being attached to active moieties (e.g., hydroxyl or amino), prevent these moieties from interference with a subsequent reaction and can be removed by conventional methods after the reaction. Examples of a hydroxyl protecting group include, but are not limited to, alkyl, benzyl, allyl, trityl (i.e., triphenylmethyl), acyl (e.g., benzoyl, acetyl, or HOOC—X"—CO—, X" being alkylene, alkenylene, cycloalkylene, or arylene), silyl (e.g., trimethylsilyl, triethylsilyl, and t-butyldimethylsilyl), alkoxylcarbonyl, aminocarbonyl (e.g., dimethylaminocarbonyl, methylethylaminocarbonyl, and phenylaminocarbonyl), alkoxymethyl, benzyloxymethyl, and alkylmercaptomethyl. Examples of an amino protecting group include, but are not limited to, alkyl, acyl, and silyl. Hydroxyl and amino protecting groups have been discussed in T. W. Greene and P. G. M. Wuts, Protective Groups in Organic Synthesis, 2nd. Ed., John Wiley and Sons (1991). Both hydroxyl and amino protecting groups can be removed by conventional methods after the reaction.

For the synthetic process described above, completion of the reaction can be monitored by any conventional method, e.g., ultra-violet spectrum, infrared spectrum, nuclear magnetic resonance, thin layer chromatography, gas chromatography, and high performance liquid chromatography. After the reaction is complete, the product can be readily used without purification due to its high yield or can be separated from the reaction mixture by one or more conventional separation methods, such as chromatography, recrystallization, extraction, or distillation. It may be further purified to give higher enantiomeric purity by methods well known in the literature. See, e.g., U.S. Pat. No. 5,223,608. The compounds of this invention may be used without purification or purified, e.g., by recrystallization using an organic solvent or chromatography.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Synthesis of Gemcitabine

(1) Purification of ethyl 3-(2,2-dimethyl-1,3-dioxolan-4-yl)-2,2-difluoro-3-hydroxypentanoate

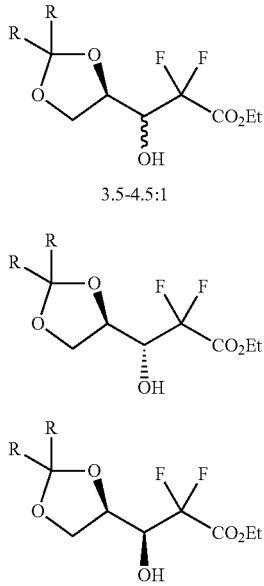

3.5-4.5:1

R = Methyl or Ethyl

Crude ethyl 3-(2,2-dimethyl-1,3-dioxolan-4-yl)-2,2-difluoro-3-hydroxypentanoate 12 (8 g) was prepared according to the method described in U.S. patent application Ser. No. 11/416,380. Before use, it was purified by silica gel chromatography eluting with hexane/CH$_2$Cl$_2$/EtOAc to give 4.6 g of (3R)-alcohol 13, 0.9 g of (3S)-alcohol 14, and 0.5 g of a mixture of the two.

(2) Preparation of 5-trityl-(3R)-hydroxy-δ-lactone (compound 1)

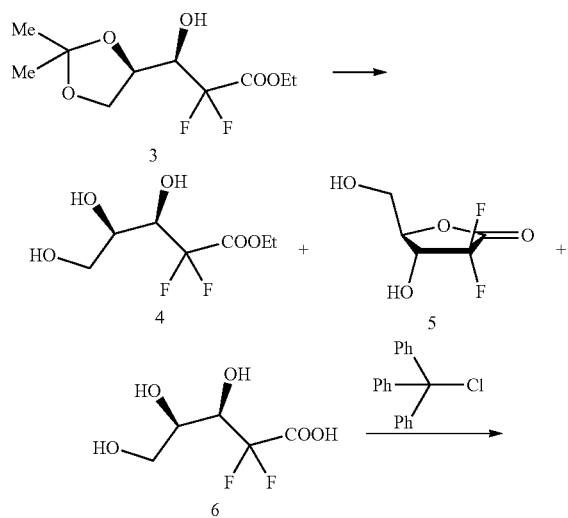

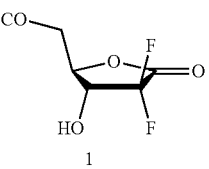

Pure (3R)-hydroxy pentanoate 3 (216 g, 850 mmol), acetonitrile (1200 mL), water (60 mL) and trifluoroacetic acid (16 mL) were charged in a 2-liter two-necked round bottom flask and then heated to 70~75° C. for 3-4 hours with stirring. The solution was cooled to ambient temperature. After the solvent was removed, the residue was azeotroped with toluene (2×100 mL).

The resulting residue was placed under vacuo. To it (including 4, 5, and 6) were added sequentially triphenylmethyl chloride (trityl chloride, 250.5 g, 1.06 equiv., 901 mmol), anhydrous EtOAc (600 mL), DMAP (1.0 g, 0.01 equiv., 8.5 mmol), and pyridine (72.9 mL, 1.06 equiv., 901 mmol) at ambient temperature. The suspension was heated to 55° C. (internal) for about 6 to 16 hours, and then cooled to 0° C. for 1 hour. The mixture was then filtered through a pad of celite and the pad was rinsed with cold EtOAc. The combined filtrate having compound 1 was used for the next step.

5-trityl-(3R)-hydroxy-2,2-difluoro δ-lactone: H$^1$NMR (CDCl$_3$): δ 3.41-3.45 (dd, 1H), 3.63-3.3.66 (dd, 1H), 4.45 (m, 1H), 4.53 (m, 1H), 7.25-7.55 (m, 15H).

(3) Preparation of 5-trityl-3-benzoyl-δ-lactone

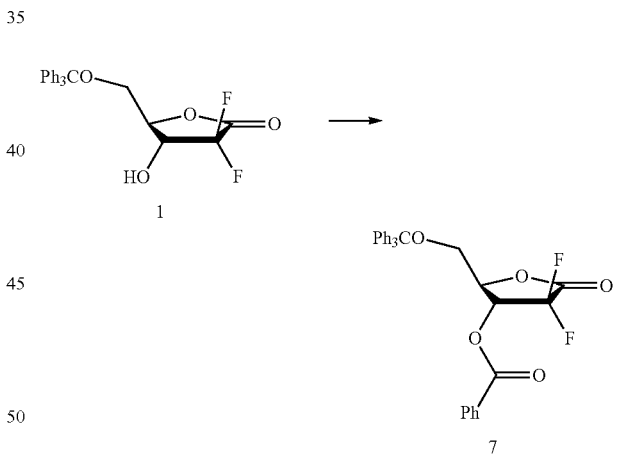

The solution of 5-trityl-δ-lactone 1 in EtOAc was cooled to 5-10° C. To this solution were sequentially added DMAP (1.0 g, 0.01 equiv., 8.5 mmol) and pyridine (78.6 mL, 1.1 equiv., 935 mmol), followed by dropwise addition of benzoyl chloride. During the addition, the internal temperature was kept at below 8° C.

The cooling bath was removed and the mixture was stirred at ambient temperature for 16 hours and then cooled to 0° C. The resulting mixture was filtered through a pad of celite and the pad was rinsed with cold EtOAc. The combined filtrate was concentrated to give 405.35 g of 5-trityl-3-benzoyl-δ-lactone 7. H$^1$ NMR (CDCl$_3$): δ 3.49-3.53 (dd, 1H), 3.67-3.3.71 (dd, 1H), 4.74 (m, 1H), 5.81 (m, 1H), 7.25-7.55 (m, 20H).

H[1] NMR (CDCl$_3$): δ 3.27 (d, 1H, OH), 3.44 (m, 2H), 4.58 (m, 1H), 5.50 (m, 1H), 5.89 (m, 1H), 7.2-8.1 (m, 20H).

(4) Preparation of (2R,3R)-4,4-difluoro-5-hydroxy-2-(trityloxymethyl)tetrahydrofuran-3-yl benzoate

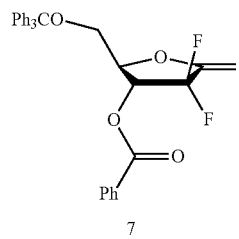

7

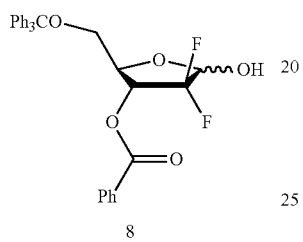

8

5-trityl-3-benzoyl-δ-lactone 7 (405.35 g, 788.6 mmol) was transferred by tert-butyl methyl ether (1970 mL) to a 5-liter two- or three-necked round bottom flask under nitrogen atmosphere. An addition funnel, attached to the 5-liter flask, was filled with Red-Al (238.83 mL, 1.06 equiv., 836 mmol). The solution was added dropwise over a period of 80 minutes to the above solution of lactone 7 at 0° C. while the internal temperature was maintained at 3-8° C.

After the addition was completed, the resulting solution was stirred for another 20 minutes. To this solution was added isopropylamine (75.5 mL, 982.5 mmol) at this temperature, followed by dropwise addition of a 20% aqueous solution of sodium titrate dibasic dihydrate (1360 mL) while the internal temperature was maintained at below 8° C. After the addition was completed, the mixture was stirred until two separate layers were observed. The aqueous layer was extracted with EtOAc (2×500 mL). The combined organic layers were washed with brine (2×100 mL), dried over MgSO$_4$, filtered and concentrated to give 395 g (765.5 mmol) of (2R,3R)-4,4-difluoro-5-hydroxy-2-(trityloxymethyl)tetrahydrofuran-3-yl benzoate 8. H[1] NMR (CDCl$_3$): δ 3.27 (d, 1H, OH), 3.44 (m, 2H), 4.58 (m, 1H), 5.50 (m, 1H), 5.89 (m, 1H), 7.2-8.1 (m, 20H).

(5) Preparation of (2R,3R)-4,4-difluoro-5-(methylsulfonyloxy)-2-(trityloxymethyl)tetrahydrofuran-3-yl benzoate

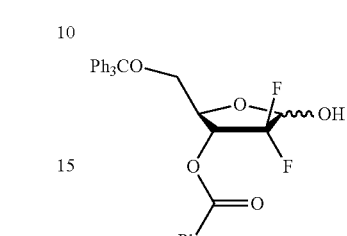

8

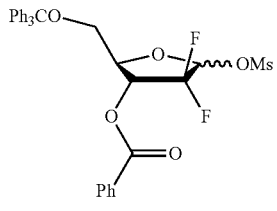

9

5-trityl-3-benzoyl lactol 8 (220 g, 426.4 mmol) and dichloromethane (880 mL) were charged into a two-necked round bottom flask at ~0° C. Et$_3$N (64.7 g, 639.6 mmol) was added to the resulting solution, followed by dropwise addition of a solution of mesyl chloride (73.2 g, 639.6 mmol) in dichloromethane (88 mL) to maintain the internal temperature at below 10° C. After the resulting solution was stirred for an additional hour, brine (200 mL) was added. The layers were separated. The organic layer was dried over MgSO$_4$, filtered, and concentrated to give 334.4 g of the crude mesylate 9. H[1] NMR (CDCl$_3$): δ 3.02 (s, 3H), 3.56 (m, 2H), 4.50 (m, 1H), 5.60 (dd, 1H), 6.03 (d, 1H), 7.21-8.15 (m, 20H).

(6) Preparation of (2R,3R)-4,4-difluoro-5-iodo-2-(trityloxymethyl)tetrahydrofuran-3-yl benzoate

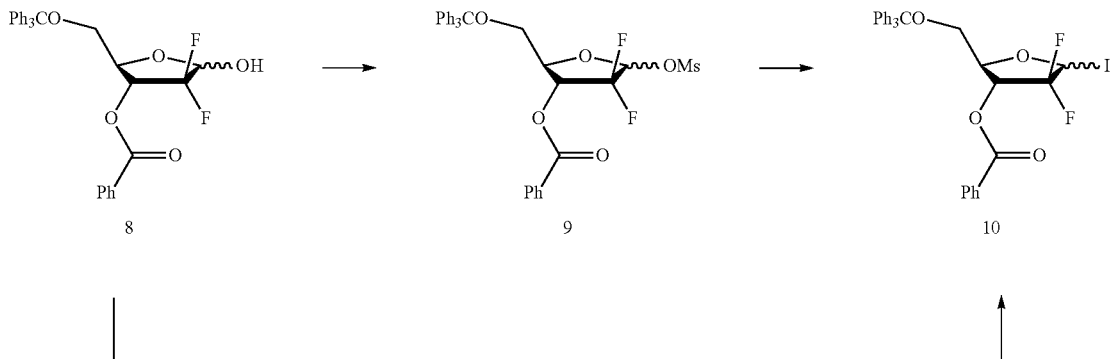

Two approaches were taken to prepare (2R,3R)-4,4-difluoro-5-iodo-2-(trityloxymethyl)tetrahydrofuran-3-yl benzoate 10 from compound 8.

Method 1:

(2R,3R)-4,4-difluoro-5-(methylsulfonyloxy)-2-(trityloxymethyl)tetrahydrofuran-3-yl benzoate 9 (2 g, 3.37 mmol), acetone (20 mL), and NaI (5 g, 33.56 mmol) were charged into a round bottom flask. The resulting mixture was refluxed for >6 hours. HPLC indicated that all starting material 9 was consumed. The reaction mixture was cooled to ambient temperature and filtered. The solvent was removed in vacuo. The residue was partitioned between dichloromethane (105 mL) and water (65 mL). The aqueous layer was extracted with dichloromethane (30 mL). The combined dichloromethane layers were washed sequentially with a 5% aqueous solution of $NaHSO_3$ (2×30 mL), a 1:1 mixture of water and brine (20 mL), and brine (2×20 mL). The solution was dried over $MgSO_4$, filtered, and concentrated to give 1.68 g of (2R,3R)-4,4-difluoro-5-iodo-2-(trityloxymethyl)tetrahydrofuran-3-yl benzoate 10. $H^1$ NMR ($CDCl_3$): δ3.44-3.57 (dd, 2H), 4.41 (m, 1H), 5.60-5.65 (dd, 1H), 6.95 (d, 1H), 7.21-8.15 (m, 20H).

Method 2:

$I_2$ (0.524 g) and dichloromethane (8 mL) were charged into a round bottom flask in the dark. To this solution was added dropwise a solution of $Ph_3P$ (0.634 g) in dichloromethane (8 mL) at ambient temperature. The resulting suspension was stirred at this temperature for 30 minutes and imidazole (0.734 g) was added. After the resulting suspension was stirred for 5 minutes at room temperature, a solution of lactol 8 (0.8 g) in dichloromethane (8 mL) was added dropwise and the resulting solution was stirred overnight at room temperature. Hexane (30 mL) was added and then the suspension was stirred for 10 minutes, filtered, and concentrated to give 1.1 g of (2R,3R)-4,4-difluoro-5-iodo-2-(trityloxymethyl)tetrahydrofuran-3-yl benzoate 10.

(7) Preparation of (2R,3R,5R)-5-(4-amino-2-oxopyrimidin-1(2H)-yl)-4,4-difluoro-2-(trityloxymethyl)tetrahydrofuran-3-yl benzoate

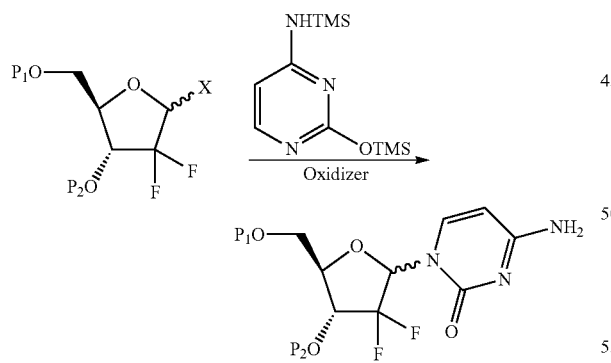

Glycosyl donor (1 g) was added to a 10 mL solution containing Di-TMS-cytosine (1.77 g) and an oxidizer (1 eq.) at 80° C.±3° C. The solvent and oxidizer used are listed in the table below. The reaction mixture was stirred for 16 hours and monitored by HPLC with a UV 230 nm detector. The solvent was removed and the product was purified by column chromatography. $H^1$ NMR ($CDCl_3$): δ3.52-3.63 (dd, 2H), 4.33 (m, 1H), 5.74 (m, 1H), 5.78 (d, 1H), 6.40 (bt, 1H), 7.21-8.15 (m, 22H). The β/α ratios of the resulting product are shown in the following table.

| Entry | P1 | P2 | X | Oxidizer | Solvent | Glycosylated cytosine anomer ratio β/α |
|---|---|---|---|---|---|---|
| 1 | Trityl | Bz | I | $NaIO_4$ | $ACN^b$ | 1.9/1 |
| 2 | Trityl | Bz | I | $DTBP^a$ | Toluene | 4.0/1 |
| 3 | Trityl | Bz | I | AIBN | Toluene | 1.3/1 |
| 4 | Trityl | Bz | I | OXONE | Toluene | 3.9/1 |
| 5 | Trityl | Bz | I | $K_2S_2O_8$ | Toluene | 5.4/1 |
| 6 | Trityl | Bz | I | $(NH_4)_2S_2O_8$ | Toluene | 5.9/1 |
| 7 | Trityl | Bz | I | $(NH_4)_2S_2O_8$ | THF | 4.5/1$^c$ |
| 8 | Trityl | Bz | I | $(NH_4)_2S_2O_8$ | ACN | 18.0/1 |
| 9 | Trityl | Bz | I | $(NH_4)_2S_2O_8$ | Toluene/ACN 5/3 | 11.4/1 |
| 10 | Trityl | Bz | Br | $(NH_4)_2S_2O_8$ | Toluene | 1.9/1 |
| 11 | Trityl | Bz | Cl | $(NH_4)_2S_2O_8$ | Toluene | 5.0/1 (2% conv.) |
| 12 | Trityl | Bz | Br | $(NH_4)_2S_2O_8$ | ACN | 4.9/1 (13% conv.) |
| 13 | Trityl | Bz | I | $K_2S_2O_8$ | ACN | 1.9/1 |
| 14 | Trityl | Bz | I | Oxone® | ACN | 2.5/1 |

$^a$DTBP = di-tert-butylperoxide
$^b$ACN = acetonitrile (8) Preparation of (2R,3R,5R)-5-(4-amino-2-oxopyrimidin-1(2H)-yl)-4,4-difluoro-2-(hydroxymethyl)tetrahydrofuran-3-yl benzoate

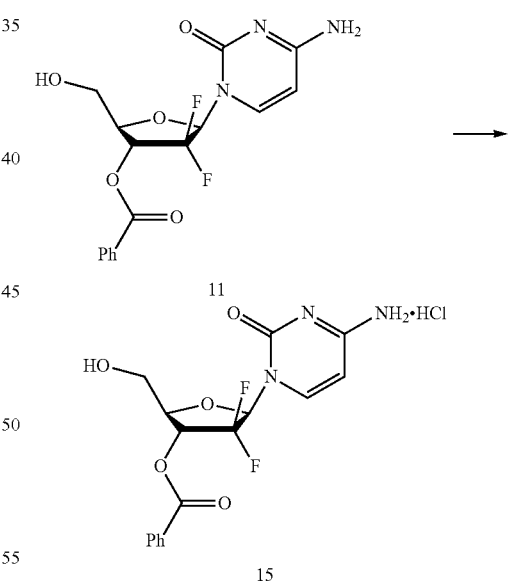

Crude compound 11 (16.3 g) and acetonitrile (20 mL) were charged into a round bottom flask. To this solution was added concentrated HCl (6 N, 3 mL) and the resulting suspension was stirred for 16 hours. The reaction mixture was filtered and then diluted with EtOAc (30 mL) at 45° C. The suspension was filtered and dried to give 3.0 g of (2R,3R,5R)-5-(4-amino-2-oxopyrimidin-1 (2H)-yl)-4,4-difluoro-2-(hydroxymethyl)tetrahydrofuran-3-yl benzoate 15 with a good β:α ratio. $H^1$ NMR (DMSO-$d_6$): δ3.73-3.84 (dd, 2H), 4.48

(m, 1H), 5.59 (m, 1H), 6.13 (d, 1H), 6.35 (t, 1H), 7.60 (m, 2H), 7.73 (t, 1H), 8.08 (m, 3H), 8.60 (bs, 1H), 9.60 (bs, 1H).

(9) Preparation of Gemcitabine

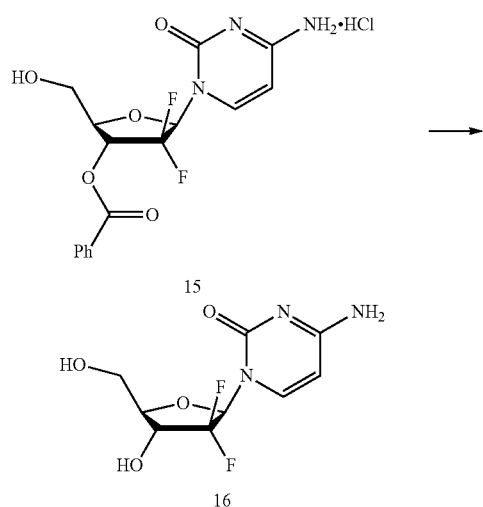

Two methods were used to convert compound 15 to compound 16.

Method 1:

Compound 15 (80.6 g, 200 mmol) and MeOH (146 mL) were charged into a round bottom flask with stirring. To this suspension was added slowly 7N $NH_3$ in MeOH (285.7 mL, 10 equiv.) and the resulting suspension was stirred overnight. The solvent was removed in vacuo. The resulting residue was dissolved in water (310 mL) with heating. The resulting aqueous solution was washed with t-butylmethylether and then layers were separated. This process was repeated several times until all organics were removed. To the aqueous solution was added charcoal (7 g) with stirring. The suspension was heated at 40° C. for 30 minutes and was filtered (without cooling) through a pad of celite. The volume was reduced to ~45 mL, and isopropylamine (180 mL) was added with stirring. To this mixture was added concentrated HCl (6 N, 105 mL) at ambient temperature with stirring. Then, the stirring suspension was cooled to and kept overnight at 0-4° C. The resulting suspension was filtered. The solid residue was washed with a cold, 4:1 mixture of isopropylamine and water (2×10 mL) and dried to give 44.25 g of gemcitabine 16. $H^1$ NMR ($D_2O$): δ3.79 (dd, 1H), 3.97 (dd, 1H), 4.05 (m, 1H), 4.30 (m, 1H), 6.16 (m, 1H), 6.22 (d, 1H), 7.95 (d, 1H).

Method 2:

Compound 15 (8.3 g, 20 mmol) and MeOH (14 mL) were charged into a round bottom flask with stirring. To this suspension were added $CF_3CH_2OH$ (5 mL) and $K_2CO_3$ (2.6 g). The resulting suspension was stirred overnight. After the solvent was removed in vacuo, the resulting residue was dissolved in water (310 mL) with heating and washed with t-butylmethylether several times. The aqueous layer was separated and treated with charcoal (0.5 g) with stirring. The suspension was heated at 40° C. for 30 minutes and was filtered (without cooling) through a pad of celite. The volume was reduced to about 5 mL and isopropylamine (2 mL) was added with stirring. To this mixture was added concentrated HCl (6 N, 10 mL) at ambient temperature. Then, the suspension was cooled to and kept overnight at 0-4° C. After filtration, the solid residue was washed with a cold, 4:1 mixture of isopropylamine and water (2×5 mL) and dried to give 4.5 g of gemcitabine 16. $H^1$ NMR ($D_2O$): δ3.79 (dd, 1H), 3.97 (dd, 1H), 4.05 (m, 1H), 4.30 (m, 1H), 6.16 (m, 1H), 6.22 (d, 1H), 7.95 (d, 1H).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent of similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A process of preparing a β-nucleoside compound formula (I):

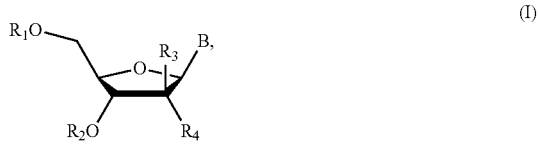

wherein each of $R_1$ and $R_2$, independently, is H, alkyl, aryl, aralkyl, alkyldiarylsilyl, trialkylsilyl, triarylsilyl, RC(O)—, RR'NC(O)—, ROC(O)—, RC(S)—, RR'NC(S)—, or ROC(S)—; each of R and R', independently, being H, alkyl, aryl, cycloalkyl, heterocycloalkyl, or heteroaryl; each of $R_3$ and $R_4$, independently, is H or fluoro; and B is

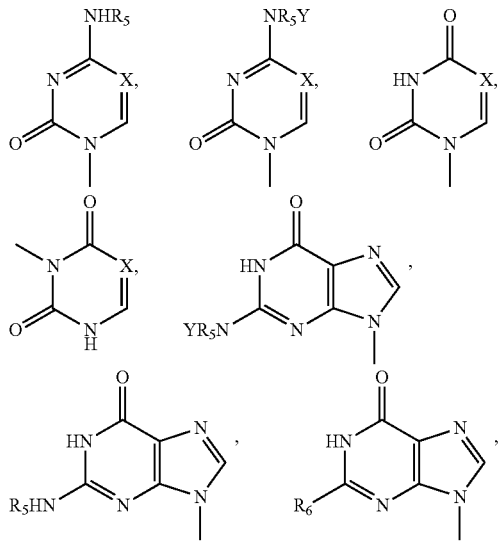

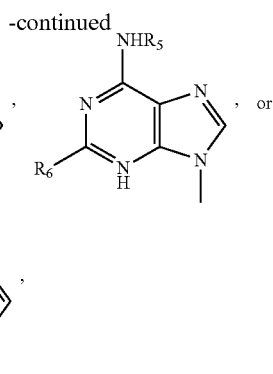

in which $R_5$ is H, alkyl, or aryl; $R_6$ is H, alkyl, alkenyl, halo, or aryl; X is N or C—R", R" being H, alkyl, alkenyl, halo, amino, or aryl; and Y is an amino protecting group;
the process comprising reacting, in the presence of an oxidizing agent, a tetrahydrofuran compound of formula (II):

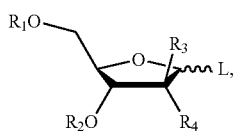

wherein $R_1$, $R_2$, $R_3$, and $R_4$ are as defined above and L is chloro, bromo, or iodio, with a nucleobase derivative of the following formula:

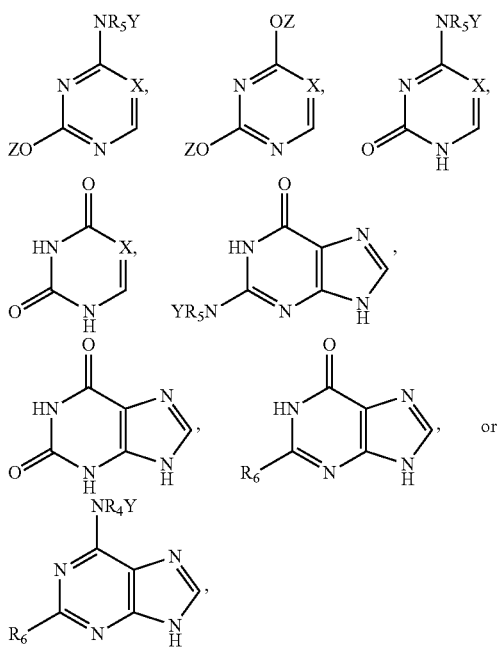

wherein $R_5$, $R_6$, X, and Y are as defined above and Z is a hydroxyl protecting group; in which the oxidizing agent is $Br_2$, $H_2O_2$, $O_2$, $Cl_2$, $O_3$, $F_2$, 3-chloroperbezoic acid, azobisisobutyronitrile, 2,2,6,6-tetramethylpiperidine 1-oxyl, or a salt including an ion selected from the group consisting of $Fe^{3+}$, $Ce^{4+}$, $Au^{3+}$, $Co^{3+}$, $NO_3^-$, $MnO_4^-$, $Cr_2O_7^{2-}$, $HSO_5^-$, and $S_2O_8^{2-}$.

2. The process of claim 1, wherein the oxidizing agent is a salt including $S_2O_8^{2-}$.

3. The process of claim 2, wherein the oxidizing agent is $(NH_4)_2S_2O_8$ or $K_2S_2O_8$.

4. The process of claim 1, wherein each of $R_3$ and $R_4$ is fluoro.

5. The process of claim 1, wherein $R_1$ is trityl and L is I.

6. The process of claim 1, wherein $R_2$ is benzoyl.

7. The process of claim 1, wherein the nucleobase derivative is

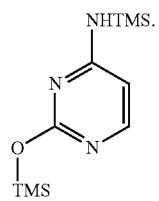

8. The process of claim 1, wherein $R_1$ is trityl, $(CH_3)_3C$, alkyldiarylsilyl, trialkylsilyl, or triarylsilyl; $R_2$ is RC(O)—, R being alkyl or aryl; and the oxidizing agent is $(NH_4)_2S_2O_8$ or $K_2S_2O_8$.

9. The process of claim 3, wherein $R_1$ is trityl and L is I.

10. The process of claim 9, wherein $R_2$ is benzoyl.

11. The process of claim 10, wherein the nucleobase derivative is

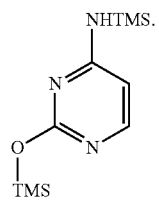

12. The process of claim 1, wherein the tetrahydrofuran compound is

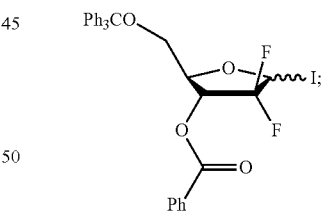

the nucleobase derivative is

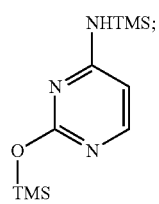

the oxidizing agent is $(NH_3)_2S_2O_8$ or $K_2S_2O_8$; and the β-nucleoside compound is

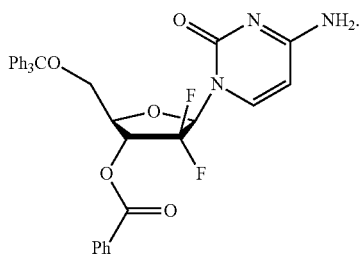

13. The process of claim 1, further comprising converting the β-nucleoside compound to a compound of formula (III):

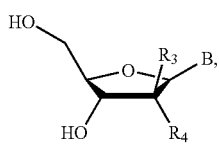
(III)

wherein $R_3$, $R_4$, and B are as defined in claim 1.

14. The process of claim 3, further comprising converting the β-nucleoside compound to a compound of formula (III):

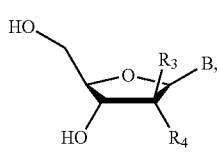
(III)

wherein $R_3$, $R_4$, and B are as defined in claim 1.

15. The process of claim 12, further comprising converting the β-nucleoside compound to the compound shown below:

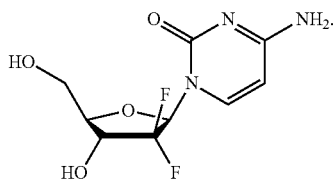

16. The process of claim 1, further comprising, before the reaction, reducing a lactone compound of the following formula (IV):

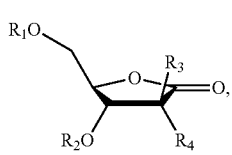
(IV)

wherein $R_3$, $R_4$, and B are as defined in claim 1, to a furanose compound of the following formula:

![Furanose formula with $R_1O$, $R_2O$, $R_3$, $R_4$, OH]

and
converting the furanose compound to the tetrahydrofuran compound of formula (II).

17. The process of claim 14, further comprising, before the reduction, treating with acid a compound of the following formula:

![Formula with $R_8O$, $R_9O$, OH, $R_4$, $R_3$, COOR$_7$]

wherein each of $R_3$ and $R_4$, independently, is H or halo; $R_7$ is H, alkyl, aryl, cycloalkyl, heteroalkyl, or heteroaryl; and each of $R_8$ and $R_9$, independently, is a H or hydroxyl protecting group, or $R_8$ and $R_9$, together, are $C_{1-3}$ alkylene;

reacting the product resulting from the above treatment with a compound of the following formula:

$R_1$-L', wherein $R_1$ is alkyl, aralkyl, alkyldiarylsilyl, trialkylsilyl, triarylsilyl, alkylcarbonyl, or arylcarbonyl; and L' is a leaving group, to produce a compound of formula (V):

![Formula V with $R_1O$, $R_3$, $R_4$, HO, O]
(V)

wherein $R_1$, $R_3$, and $R_4$ are as defined above; and
converting the compound of formula (V) to the compound of formula (IV).

18. The process of claim 17, wherein $R_2$ is benzoyl and L' is chloro, bromo, or iodo.

19. The process of claim 18, wherein $R_1$ is trityl, each of $R_3$ and $R_4$ is fluoro, and B is

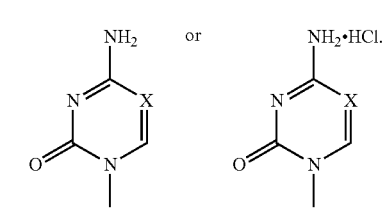

20. The process of claim 19, further comprising converting the β-nucleoside compound to a compound of formula (III):

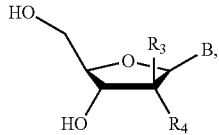

wherein each of $R_3$ and $R_4$, independently, is H or fluoro, and B is

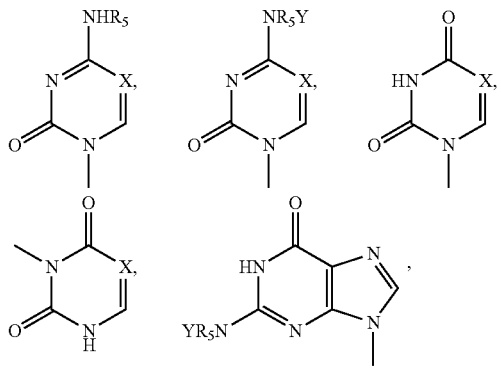

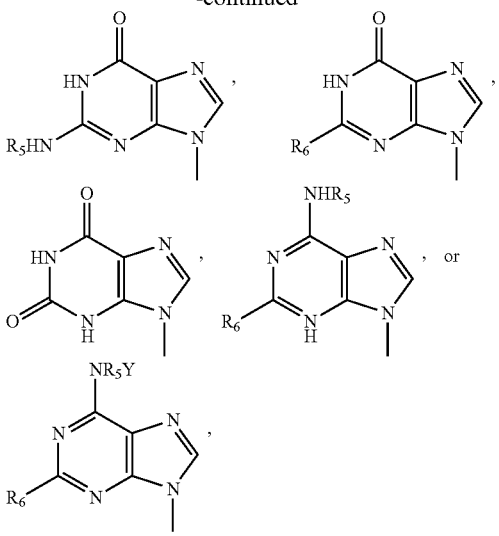

in which $R_5$ is H, alkyl, or aryl; $R_6$ is H, alkyl, alkenyl, halo, or aryl; X is N or C—R", R" being H, alkyl, alkenyl, halo, amino, or aryl; and Y is an amino protecting group.

21. The process of claim 1, wherein the reaction is conducted in a solvent of toluene.

22. The process of claim 1, wherein the reaction is conducted in a solvent containing toluene and acetonitrile.

* * * * *